United States Patent
Ek et al.

(10) Patent No.: US 12,037,241 B2
(45) Date of Patent: Jul. 16, 2024

(54) SYNTHESIS OF AMMONIUM DINITRAMIDE (ADN)

(71) Applicant: TOTALFÖRSVARETS FORSKNINGSINSTITUT, Stockholm (SE)

(72) Inventors: Stefan Ek, Tumba (SE); Jonas Johansson, Tumba (SE)

(73) Assignee: TOTALFÖRSVARETS FORSKNINGSINSTITUT, Stockholm (SE)

( * ) Notice: Subject to any disclaimer, the term of this patent is extended or adjusted under 35 U.S.C. 154(b) by 748 days.

(21) Appl. No.: 17/276,513

(22) PCT Filed: Sep. 17, 2018

(86) PCT No.: PCT/SE2018/050939
§ 371 (c)(1),
(2) Date: Mar. 16, 2021

(87) PCT Pub. No.: WO2020/060451
PCT Pub. Date: Mar. 26, 2020

(65) Prior Publication Data
US 2022/0033262 A1    Feb. 3, 2022

(51) Int. Cl.
*C01B 21/087*    (2006.01)
*B01D 9/00*    (2006.01)

(52) U.S. Cl.
CPC .......... *C01B 21/087* (2013.01); *B01D 9/0054* (2013.01); *B01D 2009/0086* (2013.01)

(58) Field of Classification Search
CPC ........................... C01B 21/087; B01D 9/0054
See application file for complete search history.

(56) References Cited

U.S. PATENT DOCUMENTS 7,981,393 B2    7/2011    Vörde et al.
10,112,834 B2 *    10/2018    Johansson ............. C01B 21/087

FOREIGN PATENT DOCUMENTS

| WO | WO 97/06099 | 2/1997 |
| WO | WO 99/46202 | 9/1999 |
| WO | WO 2015/115962 | 8/2015 |

OTHER PUBLICATIONS

Hoi-Gu Jang et al.; Scalable synthesis of high purities ammonium dinitramide and its decomposition characteristics; Journal of Industrial and Engineering Chemistry; 2018; pp. 237-244; issue 63; Elsevier B.V.
Subbiah Venkatachalam et al.; An Overview on the Synthetic Routes and Properties of Ammonium Dinitramide (AND) and other Dinitramide Salts; Propellants, Explosives, Pyrotechnics 29; 2004; pp. 178-187; No. 3; Wiley-VCH Verlag Gmbh & Co. KGaA.

\* cited by examiner

*Primary Examiner* — Yong L Chu
(74) *Attorney, Agent, or Firm* — Jacobson Holman PLLC

(57) ABSTRACT

The invention concerns a method for making ammonium dinitramide from guanylurea dinitramide in one single process step. Guanylurea dinitramide is reacted with an ammonium sulfate in a reaction solution comprising water and acetone and an ion exchange gives ammonium dinitramide. By using acetone the yield is increased compared to known processes as formed guanylurea sulfate is poorly soluable in a water-acetone solution and precipitates, while guanylurea dinitramide has higher solubility in the solution than in only water. The guanylurea sulfate precipitate formed in the reaction solution that contains acetone is less sticky than if formed in water or in a water-alcohol solution and therefore easier to filter off. The use of acetone also allows lower process temperatures to be used than in previously known methods for producing guanylurea dinitramide. Conclusively, the method gives a higher yield, demands considerable smaller amounts of solvent and allows lower process temperatures to be used than in any formerly known process.

18 Claims, No Drawings

SYNTHESIS OF AMMONIUM DINITRAMIDE (ADN)

PRESENT STATE OF TECHNOLOGY AND PROBLEMS WITH THE CURRENT PRODUCTION OF ADN

Currently, there are several known methods for making ammonium dinitramide (ADN). It can be produced by reacting guanylurea dinitramide (GUDN) in a solution of alcohol and water with potassium hydroxide which yields potassium dinitramide (KDN). The process is described in U.S. Pat. No. 7,981,393. In a second process stage KDN is reacted with ammonium sulfate in a water solution which yields ADN. The second process stage is described in EP0843647. A problem with this method is that it includes potassium. The potassium remains in the produced ADN, which is a problem, as potassium is difficult and expensive to remove from the ADN. Potassium present in ADN used as solid rockets fuels or liquid fuels presents an increased signature at combustion and creates problems with catalyst poisoning.

Another method is described in WO2015115962, hereafter called WO62. According to this method GUDN is heated together with ammonium sulfate (AS) in a water solution until the solution is homogenous. Thereafter the heat source is removed and propanol is added and this causes guanylurea sulfate (GUS) to precipitate from the solution and it can thereafter be filtered off. The filtrate contains ADN and un-reacted GUDN. The filtrate is concentrated and the residue from this stage is suspended in propanol. ADN dissolves in propanol and GUDN remains undissolved and can be discarded through filtration. The filtrate is concentrated to dryness which yields pure ADN. The problem with this process is that the GUS that is formed as a byproduct in the reaction is partly soluable in alcohol and the increasing amount of solved GUS in the reaction solution slows down the reaction rate and can even drive the reaction backwards. WO62 also describes a process in which a column is used for the ion exchange process. The new process is less time consuming.

THE INVENTION AND BENEFITS

It has been discovered that the use of acetone and water as reaction mixture for reacting GUDN with AS offers a method for producing ADN.

The invention comprises a method by which ADN can be produced using GUDN. GUDN is reacted with AS in a reaction solution of acetone and water and ADN is formed in the reaction solution through an ion exchange reaction. Yields close to 90% are possible with the method described here. The acetone increases the solubility of GUDN, which increases the yield for a certain volume of reaction mixture. GUS is poorly soluble in acetone and in aqueous acetone.

The process requires much less water than previously known processes. Replacing alcohols with acetone can double the yield, if the same ratio of acetone instead of alcohol to water is used. The amount of water can be reduced with up to 70% compared to earlier processes with maintained yield (approximately 80%). As removal of water from the product is a main contributor to the cost of ADN, any reduction of water in the process is beneficial as less energy has to be used to remove water and this reduces the production cost and in the extension also the environmental impact. Less water in the process make the production faster, which results in higher maximum production for the production plant and consequently lower cost per weight unit of the product.

The use of acetone results in a stable precipitation of GUS, which ensures that the reaction proceeds to a high yield. The guanylurea sulfate precipitate formed in the reaction solution that contains acetone is less sticky than if formed in water or in a water-alcohol solution and therefore easier to filter off.

The reaction can proceed at room temperature or lower, which both saves energy and time.

Acetone does not, in difference from alcohols that are used in previously known processes, form azeotropes with water upon evaporation. No azeotropes and a low boiling point of acetone make it easy to recycle acetone by ordinary distillation.

CLOSER DESCRIPTION OF THE INVENTION

The invention is a method for making ADN from GUDN in one single process step. GUDN is reacted with AS in a reaction solution and an ion exchange gives ADN. By the use of acetone the yield is increased compared to known processes as formed GUS is poorly soluable in a water-aceton solution, while GUDN has higher solubility in the solution than in only water, or in only acetone. The precipitation of formed GUS drives the reaction towards completion as dissolved remaining GUS may reverse the reaction and hinder the reaction to proceed to a high yield of ADN. The GUS precipitate formed in the reaction solution that contains acetone is less sticky than if formed in water or in a water-alcohol solution and therefore much easier to filter off. The use of acetone also allows lower process temperatures to be used than in previously known methods for producing GUDN. Conclusively, the method gives a higher yield, demands considerable smaller amounts of solvent and allows lower process temperatures to be used than in any formerly known process.

A beneficial alternative of the invention is that ADN can be kept in solution throughout the process. This increases the process safety, as ADN is sensitive to impact and friction as the product is not handled dry until the last stage of the process. The solution comprising ADN is dryed to obtain ADN. This alternative is described in claim 12.

Another alternative to enhance the security of the process is to concentrate the filtrate instead of drying it. ADN can then be obtained by concentration of the filtrate to such an extent that ADN precipitates, either directly or upon cooling of the solution and ADN is then obtained by filtration and drying of the resulting filter cake.

Another alternative is that the to dryness concentrated filtrate is suspended in acetone whereby the formed ADN is dissolved while any remaining GUDN remains solid and that the solid GUDN is filtered off and that ADN is obtained by concentration of the filtrate to such an extent that ADN and any remaining GUDN precipitates, either directly or upon cooling of the solution, and are obtained by filtration and drying of the resulting filter cake.

First Embodiment, Water and Acetone as Reaction Solution

In a first embodiment the reaction is made in a reaction solution that comprises both water and acetone. Acetone is easy to remove by distillation as its low boiling point is well separated from the boiling point of water and it does not form azeotropes with water. Acetone does not have to be further purified after the distillation. GUDN is added to the reaction solution and dissolves, partially or entirely, whereupon it reacts with added and dissolved AS. The solution can, in order to increase the amount of dissolved GUDN, be stirred, heated or boiled. Those methods or any other suitable method for increasing the amount of solved GUDN can be either applied alone or in any combination with any of the other. GUDN(l) reacts with AS(l), where (l) means dissolved and (s) means solid, in the solution. In the reaction ADN(l) and GUS(s) is formed. The reaction solution may also comprise unreacted GUDN(l,s) and unreacted AS(l,S). As the reaction proceeds and the formed GUS(s) precipitates remaining GUDN(s) can be dissolved as the initially dissolved GUDN is consumed in the reaction. To achieve a more complete precipitation of GUS the reaction solution can be quenched. The quenching is performed by cooling the reaction solution according to any known method or by adding cold acetone to the reaction solution. The precipitation is then removed by filtration.

The reaction can be run at room temperature, about 16-22° C., but higher temperatures, up to and involving the boiling point of the solution is also usable. GUDN is poorly soluble in water and/or acetone at or below room temperature. The higher the temperature, the more GUDN can be dissolved in the same amount of reaction solution. A higher temperature makes it thereby possible to use a smaller total amount of water for the production of a given amount of ADN. The acetone increases the solubility of GUDN which also allows a reduction of the amount of water needed for producing ADN.

GUDN is poorly soluble in pure acetone and this is therefore not a preferred alternative.

Then, subsequent to the optional quenching, the reaction solution may be further cooled in order to further enhance the precipitation of GUS. Thereafter the precipitate comprising mainly GUS, but undissolved GUDN may also be present, is filtered off. The filtrate, mainly comprising water, acetone, ADN and unreacted GUDN is concentrated. The concentration can be done by any known method to remove the water and the acetone. The water and the acetone may be separated by distillation or removed by heating and separated in a later stage to recover them.

The residue, mainly comprising ADN and GUDN is thereafter suspended in acetone or in 2-propanol. Both solvents have the advantage that GUDN is very poorly soluble in them and they therefore give a very clean filtrate of ADN after filtration.

2-propanol has the disadvantage that it dissolves less ADN per volume unit that acetone, but the advantage that it removes any remaining water by forming azeotropes with it upon concentration.

ADN can also be obtained by removing the acetone from the reaction solution by distillation and then adding 2-propanol to the residue whereafter the residue with added 2-propanol is concentrated to dryness whereafter 2-propanol is added to dissolve the formed ADN and any undissolved particles can be filtered off and ADN is obtained from the filtrate by drying it. This method yields ADN that contains less water than the other methods according to the claims.

Second Embodiment, Reaction Solution Water

The following text concerns the embodiment of a reaction solution, which comprises water and no acetone. GUDN is added to the reaction solution and dissolves, partially or entirely, whereupon it reacts with added and dissolved AS. The reaction solution may be treated with any of the following methods or combinations thereof to increase the solubility of GUDN; stirring, heating, boiling. The reaction solution comprises ADN(l), any unreacted GUDN(l,s) and a precipitation of GUS(s,l). The reaction solution can thereafter be quenched to achieve a more complete precipitation of GUS. The quenching is either done by adding cold acetone and/or cooling by any known method. The acetone and the quenching both increases the precipitation of GUS. The reaction can be run at different temperatures. Room temperature, about 16-22° C. is possible to use, but higher temperatures, up to and involving the boiling point for the reaction solution is also usable. GUDN is poorly soluble in water at or below room temperature. The higher the temperature, the more GUDN can be dissolved in the same amount of water. A higher temperature makes it possible to use a smaller total amount of water for the production of a given amount of ADN.

Then, subsequent to the adding of acetone, the reaction solution may be cooled in order to further enhance the precipitation of GUS. Thereafter the precipitate, comprising mainly GUS, but undissolved GUDN may also be present, is filtered off. The filtrate, mainly comprising water, acetone, ADN and GUDN is concentrated by any known method to remove the water and acetone as described in the first embodiment.

The residue, mainly comprising ADN and GUDN, is thereafter suspended in acetone or in 2-propanol. Both solvents have the advantage that GUDN is very poorly soluable in them and therefore gives a very clean solution of ADN in the solvent after filtration. 2-propanol has the disadvantage that it dissolves less ADN per volume unit that acetone but the advantage that it removes water by forming azeotropes with it upon concentration.

ADN can also be obtained by removing the acetone from the reaction solution by distillation and then adding 2-propanol to the residue whereafter the residue with added 2-propanol is concentrated to dryness whereafter 2-propanol is added to dissolve the formed ADN and any undissolved particles can be filtered off and ADN is obtained from the filtrate by drying it. This method yields ADN that contains less water than the other methods according to the claims.

EXAMPLES

Example 1

GUDN (10 g), ammonium sulfate (7.84 g), water (25 ml), and acetone (50 ml) were refluxed under stirring for 30 min Cold acetone (100 ml, ~0° C.) was added to the reaction mixture. The resulting suspension was cooled to 10° C. and then filtered to remove solid precipitated GUS. The filtrate contained GUDN(l) and ADN(l) and it was concentrated to dryness. The residue was suspended in acetone (30 ml). The undissolved particles, GUDN, were removed by filtration. The resulting filtrate was concentrated to dryness. This produced 4.69 g (79.5%) pure ADN.

Example 2

GUDN (10 g), ammonium sulfate (7.84 g), water (50 ml), and acetone (100 ml) were stirred at room temperature for 60 min. The acetone was removed by distillation. 2-propanol (550 ml) was added to the residue. The mixture was concentrated to dryness. The residue was suspended in 2-propanol (100 ml). The undissolved particles were removed by filtration. The resulting filtrate was concentrated to dryness. This produced 4.71 g (79.8%) pure ADN.

Example 3

GUDN (10 g), ammonium sulfate (7.84 g), and water (25 ml) were heated under stirring until a homogenous solution was obtained. This happened at approximate 85° C. This solution was poured into cold acetone (−78° C., 400 ml). The cooling continued until the mixture had a temperature of approximately −20° C. It was then passed through a cooled filter to remove any solids. The filtrate was concentrated to dryness. The residue was suspended in 2-propanol (150 ml). The undissolved particles were removed by filtration. The resulting filtrate was concentrated to dryness. This produced 5.25 g (89.0%) pure ADN.

TABLES

The investigated experimental conditions are shown in the tables below. In all cases 10 grams of GUDN were used.

In columns 1 and 2 the volumes of the water and the acetone that were used in the reactions are shown in ml.

In column 3 the total volume of water and acetone is shown, which is the sum of column 1 and 2.

In column 4 the yield of ADN is shown.

In column 5 the reaction temperature is shown.

In column 6 the reaction time is shown.

In column 7 the volume of the acetone that was used for quenching is shown.

In column 8 the temperature of the acetone that was used for quenching is shown.

In column 9 the temperature of the reaction solution at filtration is shown.

In column 10 the molar ratio of AS/GUDN is shown.

TABLE 1

| 1. $H_2O$ (ml) | 2. Acetone (ml) | 3. Total volume (ml) | 4. Yield (%) | 5. Reaction Temp. (° C.) | 6. Reaction Time (min) | 7. Quench volume (ml) | 8. Temp. of quench medium (° C.) | 9. Filtration Temp (° C.) | 10. Eq. Of AS |
|---|---|---|---|---|---|---|---|---|---|
| 10 | 20 | 30 | 28.8 | 65 | 30 | 100 | RT | 10 | 1.3 |
| 20 | 40 | 60 | 59.8 | 65 | 30 | 100 | RT | 10 | 1.3 |
| 25 | 50 | 75 | 79.5 | 65 | 30 | 100 | RT | 10 | 1.3 |
| 30 | 60 | 90 | 80.2 | 65 | 30 | 120 | RT | 10 | 1.3 |
| 50 | 100 | 150 | 83.1 | 65 | 30 | 250 | RT | 14 | 1.3 |

In table 1 the effect of the amount of solvent at the water to acetone ratio 1:2 is shown. It shows that the yield increases with the amount of solvent, but the gain from the use of more than 25 ml of water is little.

TABLE 2

| 1. $H_2O$ (ml) | 2. Acetone (ml) | 3. Total volume (ml) | 4. Yield (%) | 5. Reaction Temp. (° C.) | 6. Reaction Time (min) | 7. Quench volume (ml) | 8. Temp. of quench medium (° C.) | 9. Filtration Temp (° C.) | 10. Eq. Of AS |
|---|---|---|---|---|---|---|---|---|---|
| 10 | 50 | 60 | 30.0 | 64 | 60 | 100 | RT | 35 | 1.3 |
| 20 | 40 | 60 | 59.8 | 65 | 30 | 100 | RT | 10 | 1.3 |
| 30 | 30 | 60 | 73.2 | 65 | 30 | 100 | RT | 10 | 1.3 |

In table 2 the effect of the ratio of water to acetone is shown. It shows that the yield increases with the amount of water.

TABLE 3

| 1. $H_2O$ (ml) | 2. Acetone (ml) | 3. Total volume (ml) | 4. Yield (%) | 5. Reaction Temp. (° C.) | 6. Reaction Time (min) | 7. Quench volume (ml) | 8. Temp. of quench medium (° C.) | 9. Filtration Temp (° C.) | 10. Eq. Of AS |
|---|---|---|---|---|---|---|---|---|---|
| 100 | 0 | 100 | 89.0 | 85 | 5-10 | 400 | −78 | −22 | 1.3 |
| 100 | 0 | 100 | 85.3 | 85 | 5-10 | 400 | −70 | −12 | 1.3 |
| 100 | 0 | 100 | 83.6 | 85 | 5-10 | 400 | 0 | 10 | 1.3 |
| 100 | 0 | 100 | 81.5 | 85 | 5-10 | 400 | 0 | 20 | 1.3 |

In table 3 the effect of the filtration temperature is shown. It shows that the reaction may be performed in pure water. It also shows that the yield is decreased with higher temperatures, but that the loss due to temperature is little. Higher and lower temperatures than shown in the table are possible, but not interesting as higher temperatures probably give a lower yield and lower temperatures are not practically to use compared to the gain in yield that they might offer.

TABLE 4

| 1. H$_2$O (ml) | 2. Acetone (ml) | 3. Total volume (ml) | 4. Yield (%) | 5. Reaction Temp. (° C.) | 6. Reaction Time (min) | 7. Quench volume (ml) | 8. Temp. of quench medium (° C.) | 9. Filtration Temp (° C.) | 10. Eq. Of AS |
|---|---|---|---|---|---|---|---|---|---|
| 50 | 100 | 150 | 74.4 | RT | 90 | 250 | RT | 10 | 0.5 |
| 50 | 100 | 150 | 77.3 | RT | 90 | 250 | RT | 25 | 1.3 |
| 50 | 100 | 150 | 82.9 | RT | 90 | 250 | RT | 25 | 2 |
| 50 | 100 | 150 | 82.3 | RT | 90 | 250 | RT | 25 | 5 |

In table 4 the effect of the amount of AS in the reaction solution is shown. The reaction starts as soon as any AS is added, but less than 0.5 equivalents is not useful since that is the smallest amount required to allow full conversion. The yield increases with the amount of AS, but levels off after two equivalents. It is possible but not useful to use more AS.

TABLE 5

| 1. H$_2$O (ml) | 2. Acetone (ml) | 3. Total volume (ml) | 4. Yield (%) | 5. Reaction Temp. (° C.) | 6. Reaction Time (min) | 7. Quench volume (ml) | 8. Temp. of quench medium (° C.) | 9. Filtration Temp (° C.) | 10. Eq. Of AS |
|---|---|---|---|---|---|---|---|---|---|
| 50 | 50 | 100 | 80.0 | 64 | 5-10 | 250 | RT | 15 | 1.3 |
| 50 | 50 | 100 | 71.9 | 25 | 90 | 250 | RT | 15 | 1.3 |

In table 5 the influence of the reaction temperature is shown. It can be noted that even with much longer reaction time the yield is lower at room temperature than at the boiling point of the mixture. Lower reaction temperature is possible, but not useful, as that would further prolong the reaction time. Shorter reaction times are also possible, but not useful, as that will decrease the yield.

TABLE 6

| 1. H$_2$O (ml) | 2. Acetone (ml) | 3. Total volume (ml) | 4. Yield (%) | 5. Reaction Temp. (° C.) | 6. Reaction Time (min) | 7. Quench volume (ml) | 8. Temp. of quench medium (° C.) | 9. Filtration Temp (° C.) | 10. Eq. Of AS |
|---|---|---|---|---|---|---|---|---|---|
| 50 | 25 | 125 | 39.5 | RT | 90 | 400 | RT | 25 | 1.3 |
| 50 | 50 | 100 | 71.9 | RT | 90 | 300 | RT | 25 | 1.3 |
| 50 | 100 | 150 | 77.3 | RT | 90 | 250 | RT | 25 | 1.3 |
| 50 | 150 | 200 | 79.9 | RT | 90 | 200 | RT | 25 | 1.3 |

In table 6 the influence of the amount of acetone in a reaction mixture with a specific amount of water is shown. The yield increases with the amount of acetone. The gain from 100 ml to 150 ml is small. Larger volumes of acetone are possible, but not useful, as this would require very large reactors.

The invention claimed is:

1. A method for producing ammonium dinitramide in which guanylurea dinitramide is reacted with ammonium sulfate in a reaction solution comprising water, and that in said reaction solution ammonium dinitramide and guanylurea sulfate is formed whereby the guanylurea sulfate precipitates characterized in that acetone is added to the reaction solution to increase the precipitation of guanylurea sulfate and also to increase the amount of dissolved guanylurea dinitramide to increase the yield of ammonium dinitramide formed in the reaction solution.

2. The method according to claim 1 characterized in that the reaction solution is filtrated to remove formed precipitated guanylurea sulfate and that the filtrate is concentrated to dryness and then the residue is suspended in acetone whereby the formed ammonium dinitramide is dissolved while any remaining guanylurea dinitramide remains solid and can be filtered off and ammonium dinitramide is obtained by concentration of the filtrate to dryness.

3. The method according to claim 1 characterized in that the reaction solution is filtrated to remove formed precipitated guanylurea sulfate and that the filtrate is concentrated to dryness and then the residue is suspended in 2-propanol whereby the formed ammonium dinitramide is dissolved while any remaining guanylurea dinitramide remains solid and can be filtered off and ammonium dinitramide is obtained by concentration of the filtrate to dryness.

4. A method for producing ammonium dinitramide characterized in that guanylurea dinitramide is reacted with ammonium sulfate in a reaction solution comprising water and acetone, in which reaction solution ammonium dinitramide forms and from which solution guanylurea sulfate precipitates.

5. The method according to claim 4 characterized in that the reaction solution is heated and/or refluxed and/or stirred in order to increase the solubility of guanylurea dinitramide and thereby increasing the yield of ammonium dinitramide.

6. The method according to claim 4 characterized in that the reaction solution is cooled to reduce the solubility of the guanylurea sulfate formed and make it precipitate from the reaction solution.

7. The method according to claim 4 characterized in that acetone is added to the reaction solution to reduce the solubility of guanylurea sulfate formed and make it precipitate from the reaction solution.

8. The method according to claim 4 characterized in that the reaction solution is filtrated to remove the precipitated guanylurea sulfate and any possible remaining guanylurea dinitramide and/or ammonium sulfate and that the filtrate, comprising ammonium dinitramide and any remaining guanylurea dinitramide is concentrated to dryness after the filtration.

9. The method according to claim 8 characterized in that the to dryness concentrated filtrate is suspended in acetone whereby the formed ammonium dinitramide is dissolved while any remaining guanylurea dinitramide remains solid and that the solid guanylurea dinitramide is filtered off and that the filtrate is concentrated to dryness whereby ammonium dinitramide is obtained.

10. The method according to claim 8 characterized in that the to dryness concentrated filtrate is suspended in 2-propanol whereby the ammonium dinitramide is dissolved while any remaining guanylurea dinitramide remains solid and can be filtered off and that the filtrate is concentrated to dryness whereby ammonium dinitramide is obtained.

11. The method for producing ammonium dinitramide according to claim 1 characterized in that the acetone in the reaction solution is removed by distillation, whereafter 2-propanol is added to the residue, whereafter the residue with added 2-propanol is concentrated to dryness, whereafter 2-propanol is added to dissolve the formed ammonium dinitramide and any undissolved particles can be filtered off and ammonium dinitramide is obtained from the filtrate by concentrating it to dryness.

12. The method for producing ammonium dinitramide according to claim 1 characterized in that the acetone in the reaction solution is removed by distillation, whereafter 2-propanol is added to the residue, whereafter the residue with added 2-propanol is evaporated to remove any remaining water, whereafter the residue is filtrated to remove any undissolved particles and ammonium dinitramide is obtained from the filtrate by concentrating it to dryness.

13. The method according to claim 1 characterized in that the reaction solution is filtrated to remove formed precipitated guanylurea sulfate and that the filtrate is concentrated to dryness and then the residue is suspended in acetone whereby the formed ammonium dinitramide is dissolved while any remaining guanylurea dinitramide remains solid and can be filtered off and ammonium dinitramide is obtained by concentration of the filtrate to such an extent that ammonium dinitramide precipitates, either directly or upon cooling of the solution, and is obtained by filtration and drying of the resulting filter cake.

14. The method according to claim 1 characterized in that the reaction solution is filtrated to remove formed precipitated guanylurea sulfate and that the filtrate is concentrated to dryness and then the residue is suspended in 2-propanol whereby the formed ammonium dinitramide is dissolved while any remaining guanylurea dinitramide remains solid and can be filtered off and ammonium dinitramide is obtained by concentration of the filtrate to such an extent that ammonium dinitramide precipitates, either directly or upon cooling of the solution, and is obtained by filtration and drying of the resulting filter cake.

15. The method according to claim 8 characterized in that the to dryness concentrated filtrate is suspended in acetone whereby the formed ammonium dinitramide is dissolved while any remaining guanylurea dinitramide remains solid and that the solid guanylurea dinitramide is filtered off and that ammonium dinitramide is obtained by concentration of the filtrate to such an extent that ammonium dinitramide and any remaining guanylurea dinitramide precipitates, either directly or upon cooling of the solution, and are obtained by filtration and drying of the resulting filter cake.

16. The method according to claim 8 characterized in that the to dryness concentrated filtrate is suspended in 2-propanol whereby the ammonium dinitramide is dissolved while any remaining guanylurea dinitramide remains solid and can be filtered off and that ammonium dinitramide is obtained by concentration of the filtrate to such an extent that ammonium dinitramide precipitates, either directly or upon cooling of the solution, and is obtained by filtration and drying of the resulting filter cake.

17. The method for producing ammonium dinitramide according to claim 1 characterized in that the acetone in the reaction solution is removed by distillation, whereafter 2-propanol is added to the residue, whereafter the residue with added 2-propanol is concentrated to dryness, whereafter 2-propanol is added to dissolve the formed ammonium dinitramide and any undissolved particles can be filtered off and ammonium dinitramide is obtained by concentration of the filtrate to such an extent that ammonium dinitramide precipitates, either directly or upon cooling of the solution, and is obtained by filtration and drying of the resulting filter cake.

18. The method for producing ammonium dinitramide according to claim 1 characterized in that the acetone in the reaction solution is removed by distillation, whereafter 2-propanol is added to the residue, whereafter the residue with added 2-propanol is evaporated to remove any remaining water, whereafter the residue is filtrated to remove any undissolved particles and ammonium dinitramide is obtained by concentration of the filtrate to such an extent that ammonium dinitramide precipitates, either directly or upon cooling of the solution, and is obtained by filtration and drying of the resulting filter cake.

* * * * *